United States Patent [19]

Langer et al.

[11] Patent Number: 5,023,266
[45] Date of Patent: Jun. 11, 1991

[54] METHOD OF TREATMENT OF PSYCHOTIC DISORDERS

[75] Inventors: Salomon Z. Langer, Paris; Jonathan R. Frost, Wissous; Johannes Schoemaker, Gif sur Yvette; Bernard Gaudilliere, Nanterre; Jean Bertin, Clamart; Jean Rousseau, Bourg-la-Reine; Régis Dupont, Tours; Alexander E. Wick, St Nom la Bretéche, all of France

[73] Assignee: Synthelabo, Paris, France

[21] Appl. No.: 469,783

[22] Filed: Jan. 24, 1990

[30] Foreign Application Priority Data

Nov. 14, 1989 [FR] France .................... 89 14868

[51] Int. Cl.$^5$ ............................ A61K 31/445
[52] U.S. Cl. .................................... 514/317
[58] Field of Search .......................... 514/317

[56] References Cited

U.S. PATENT DOCUMENTS 4,690,931  9/1987  Wick et al. .................... 514/317

OTHER PUBLICATIONS

M. B. Bowers, Jr., "Clinical Phenomenology in the Functional Psychoses", Biology of the Major Psychoses, D. X. Friedman (ed.), vol. 54, pp. 1–8 (1975).
Ross J. Baldessarini, Drugs and the Treatment of Psychiatric Disorders, in Alfred Goodman Gilman, Louis S. Goodman, Theodore W. Rall, Ferid Murad (editors), The Pharmacological Basis of Therapeutics, 7th edition, 1985, pp. 387–445.

Primary Examiner—Stanley J. Friedman
Attorney, Agent, or Firm—Wegner, Cantor, Mueller & Player

[57] ABSTRACT

Ifenprodil and its analogues are useful for the treatment of psychoses such as schizophrenia.

8 Claims, No Drawings

METHOD OF TREATMENT OF PSYCHOTIC DISORDERS

The present invention is directed to the use of Ifenprodil and analogues thereof in a method for the treatment of psychotic disorders.

The compounds to be used correspond to general formula (I) below, wherein $R_1$ denotes a halogen atom or a hydroxy group, $R_2$ denotes a hydrogen atom or a methyl group, and $R_3$ denotes a hydrogen or halogen atom.

According to whether R2 de h or methyl, the compounds of general formula (I) comprises one or two chiral centers. The compounds can hence exist in various stereochemical forms. TheY can exist also in the form of free bases or acid addition salts.

The compounds of general formula (I) are disclosed in U.S. Pat. No. 3,509,164, in French patent 2546166, in European patent 0109317, in French patent 2628740, and in C.A., 94, 83708b (1981).

The compounds have been submitted to pharmacological tests showing their antipsychotic activity.

In particular their inhibitory activity on the binding of [³H](+)3(3-hydroxyphenyl)-N-(1-propyl)-piperidine, or [³H]-(+)-3-PPP, to the σ-receptor in the cerebral cortex of rats has been studied, essentially as described in J. Pharmacol. Exp. Ther., 238, 739-748, (1986). Male Sprague-Dawley rats (150-200 g) were sacrificed, and the cerebral cortex was homogenized in 25 volumes of ice-cold Tris-HCl buffer (pH 7.4 at 25° C.) with the use of an Ultra-Turrax ™ polytron. The homogenate was washed twice by centrifugation (10 min at 45,000g) and intermittent resuspension of the resulting pellet in fresh buffer. The final pellet was resuspended in 20 volumes of 50mM Tris-HCl buffer (pH 8.0 at 22° C.). A 75 µl aliquot of this membrane preparation was then incubated in a final volume of 250 µl with 2nM [³H]-(+)-3-PPP (specific activity 90 Ci/mmol; New England Nuclear) for 90 min at 25° C., in the absence or in the presence of competing drugs. After incubation, the membranes were recovered by filtration over 0.05% polyethyleneimine-pretreated Whatman ™ GF/B filters using a Skatron ™ Cell Harvester, and washed with ±2.5 ml of ice-cold 50mM Tris-HCl buffer (pH 7.7 at 0° C.). Non-specific binding was defined with 1µM haloperidol.

Data were analyzed by conventional graphical techniques and least-squares regression analysis where appropriate.

The following Table indicates the $IC_{50}$ of the compounds, i.e. the concentration (µM) which inhibits 50 percent of the [³H]-(+)-3-PPP.

TABLE

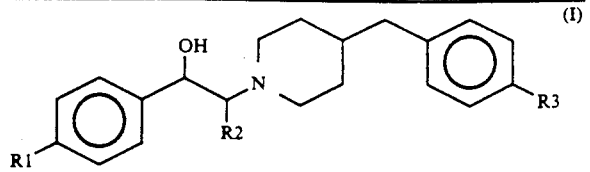

(I)

| N° | R1 | R2 | R3 | Form | Salt or base | $IC_{50}$ |
|---|---|---|---|---|---|---|
| 1 | OH | CH₃ | H | (±) erythro | HCl | 0.008 |
| 2 | OH | CH₃ | H | (±) threo | base | 0.01 |
| 3 | OH | CH₃ | H | (−) erythro | Bz. | 0.015 |
| 4 | OH | CH₃ | H | (+) erythro | Bz. | 0.007 |
| 5 | Cl | H | F | (±) | HCl | 0.003 |
| 6 | Cl | H | F | (+) | base | 0.0092 |
| 7 | Cl | H | F | (−) | base | 0.0098 |

Note: "HCl" denotes the hydrochloride salt, and "Bz." denotes the benzoate salt.

The results of the pharmacological tests show that the compounds of general formula (I) have high affinity for the σ-receptor, and that they are potential antipsychotics for the human.

Therefore they are useful for the treatment of psychoses, and especially of schizophrenia.

They can be presented in any form suitable for enteral or parenteral administration, in combination with any suitable excipient, for example in the form of tablets, gelatin capsules, capsules, oral or injectable solutions or suspensions.

The daily dosage can range from 1 to 120 mg of active substance.

We claim:

1. A method of treatment of schizophrenia-like psychoses in humans, which comprises administering to a patient in need thereof an antipsychotically effective amount of a compound of general formula (I)

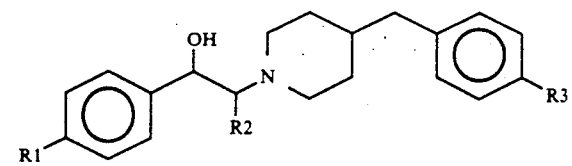

wherein R1 denotes a halogen atom or a hydroxy group, R2 denotes a hydrogen atom or a methyl group, and R3 denotes a hydrogen or halogen atom,
   said compound being a pure optical isomer or a mixture of optical isomers, in the form of either a free base or a pharmaceutically acceptable addition salt.

2. The method according to claim 1, wherein the compound is (±)erythro-α-(4-hydroxyphenyl)-β-methyl-4-(phenylmethyl)-1-piperidineethanol.

3. The method according to claim 1, wherein the compound is (±)threo-α-(4-hydroxyphenyl)-β-methyl-4-(phenylmethyl)-1-piperidineethanol.

4. The method according to claim 1, wherein the compound is (+)erythro-α-(4-hydroxyphenyl)-β-methyl-4-(phenylmethyl)-1-piperidineethanol.

5. The method according to claim 1, wherein the compound is (−)erythro-α-(4-hydroxyphenyl)-β-methyl-4-(phenylmethyl)-1-piperidineethanol.

6. The method according to claim 1, wherein the compound is (±)-α-(4-chlorophenyl)-4-[(4-fluorophenyl)methyl]-1-piperidineethanol.

7. The method according to claim 1, wherein the compound is (+)-α-(4-chlorophenYl)-4-[(4-fluorophenyl)methyl]-1-piperidineethanol.

8. The method according to claim 1, wherein the compound is (−)-α-(4-chlorophenyl)-4-[(4-fluorophenyl)methyl]-1-piperidineethanol.

* * * * *